United States Patent
Wilhelm

[11] Patent Number: 5,190,878
[45] Date of Patent: Mar. 2, 1993

[54] APPARATUS FOR CULTIVATING CELLS

[76] Inventor: Minuth Wilhelm, Neue Welt 1, 8401 Hohengebraching, Fed. Rep. of Germany

[21] Appl. No.: 627,729

[22] Filed: Dec. 14, 1990

[30] Foreign Application Priority Data

Jul. 14, 1989 [DE] Fed. Rep. of Germany ....... 3923279

[51] Int. Cl.⁵ .................. C12M 3/00; C12M 3/04; C12M 1/14
[52] U.S. Cl. .................................. 435/285; 435/284; 435/310
[58] Field of Search ............... 435/170–180, 435/240.1–240.243, 284–287, 296–301, 310–311, 313

[56] References Cited

U.S. PATENT DOCUMENTS

| | | | |
|---|---|---|---|
| 2,761,813 | 9/1956 | Goetz | 435/299 |
| 3,839,155 | 10/1974 | McAleer et al. | 435/285 |
| 4,087,327 | 5/1978 | Feder et al. | 435/250.241 |
| 4,172,013 | 10/1979 | Skoda et al. | 435/285 |
| 4,225,671 | 9/1980 | Puchinger et al. | 435/285 |
| 4,228,243 | 10/1980 | Iizuka | 435/285 |
| 4,242,459 | 12/1980 | Chick et al. | 435/284 |
| 4,446,234 | 5/1984 | Russo et al. | 435/284 |
| 4,608,342 | 8/1986 | Nees | 435/240 |
| 4,656,130 | 4/1987 | Shoshan | 435/286 |
| 4,661,455 | 4/1987 | Hubbard | 435/285 |
| 4,661,458 | 4/1987 | Berry et al. | 435/285 |
| 4,681,853 | 7/1987 | Hardy et al. | 435/285 |
| 4,748,124 | 5/1988 | Vogler | 435/285 |
| 4,762,794 | 8/1988 | Nees | 435/285 |
| 4,835,102 | 5/1989 | Bell et al. | 435/284 |
| 4,937,196 | 6/1990 | Wrasidlo et al. | 435/284 |

FOREIGN PATENT DOCUMENTS 303294 2/1989 European Pat. Off. .

Primary Examiner—Robert J. Warden
Assistant Examiner—T. A. Trembley
Attorney, Agent, or Firm—Lucas & Just

[57] ABSTRACT

The apparatus uses a holding device (2) which has a support ring (3) and a fixed ring (4). A cell substrate (1) is held between support ring (3) and fixed ring (4). The fixed ring (4) has a thickness less than the cylindrical height (3') of the support ring (3) so that only the support ring abuts against the surface of the culture vessel. Since fixing ring (4) does not abut against a surface, there is no pressure on the cell substrate (1). The holding device (2) is held inside the apparatus with space on both the apical and basal sides. Inflow ports (13) and outflow ports (14) are provided for both apical space and basal space to allow for introduction of cell treatment medium.

15 Claims, 5 Drawing Sheets

APPARATUS FOR CULTIVATING CELLS

BACKGROUND OF THE INVENTION

It is generally known that during cell cultivation in biological and biotechnological experiments the composition of the extracellular biomatrix is of very great importance for the attachment and specific differentiation performance of the respective cells. Such an extracellular matrix consists, among other things, of different collagens, laminin, fibropectin and other collagen-like or non-collagen-like proteins. In many experiments it was found that highly specialized cells cannot be cultivated without such a substrate material.

So far, besides the microcarrier technique, there are only a few auxiliary means permitting the cultivation of live cells on supports. These include hollow cylinders with a filter material placed on one side thereof, and on which cells can grow. Furthermore it is known that a confluent cell layer can be cultivated on a porous or semipermeable substrate, in which case the substrate in disk-shaped form must be clamped in an annular holding device, which, stabilized in this manner, is placed in the appropriate culture vessel (U.S Pat. No. 4,608,342).

SUMMARY OF THE INVENTION

The object of the invention is to develop an apparatus for the cultivation of cells, in which the cells can be kept under conditions that are as natural as possible (continuous perfusion) and in which the cultivated material can be rapidly transferred from one experimental arrangement to another.

Proposed for this purpose according to the invention is an apparatus for the cultivation of cells, with a culture vessel forming an inner space or a chamber and having, for a treatment medium, at least one inflow opening communicating with the inner space and at least one outflow opening communicating with the inner space, as well as having at least one exchangeable cell substrate in the culture vessel. Arranged as cell substrate in the inner space of the culture vessel is at least one lamellar or film-like cell support for the cells, which (cell support) is fixed in a frame-like holding device, the arrangement being such that the treatment medium can act upon the cell support from the apical and basal side.

In this arrangement the cells grow in a special culture vessel with inflow and outflow opening for at least one treatment medium, on a single cell support (FIG. 3) or simultaneously on several exchangeable, lamellar or film-like cell supports (FIG. 4). This technique permits the cultivation of highly differentiated cells on a small laboratory scale, or, by arbitrarily increasing the size of the cell supports, on an increasingly larger scale, as e.g. in bioreactors. Moreover this technique makes it possible to carry out a consistent biotechnical scale-up while using always the same working materials.

The respective treatment medium is a gaseous or liquid medium. Treatment media or culture media within the meaning of the invention are, in particular, life-supporting, differentiation-promoting substances, as well as substances which stimulate biomaterial formation (e.g. formation of viruses).

Below, the invention will be explained in detail by means of examples based on the Figures.

DETAILED DESCRIPTION OF THE INVENTION

Figure 1:
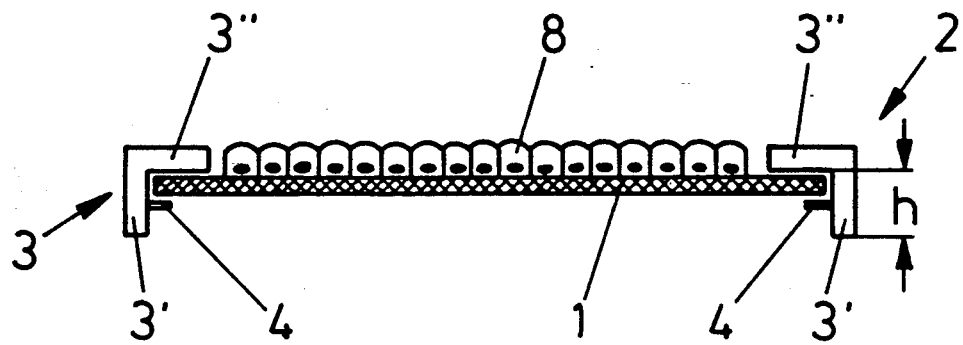
FIG. 1 is a simplified representation in cross-sectional view of a holding device with a cell support fixed in said holding device and with cells cultivated on the cell support.

In the Figures the numeral 1 represents a cell support made of sheet material. It is obtained by cutting, punching, etc. from a suitable material such as film, filter, mesh, fibrous sheet material, spongy (foam-like) sheet material or another suitable support material, as well as by possible coating with a cellular or extracellular matrix product. The cell support 1, which in the embodiment shown has a circular disk shape, is then fixed in a holding device 2 which consists of a supporting ring 3 and a fixing ring 4. The one-piece supporting ring 3 consists of a circular-cylinder-shaped or hollow-cylinder-shaped section 3' and a section 3". The latter forms an inwardly directed annular flange which is provided on a front side of the section 3'.

The fixing ring 4, which has essentially the form of a flat ring, is placed in the supporting ting 3 and held by clamp fit in section 3', so that the cell support 1 is clamped in the region of its peripheral edge between the section 3" and the fixing ring 4. The thickness of the fixing ring 4 in the direction of the axis of the supporting ring and of the fixing ring 4 is several times smaller than the axial height h of the section 3', this axial height h being the distance between the free edge—in FIG. 1 the lower edge—of the section 3' and the section 3". As a result of the small thickness of the fixing ring 4 relative to the height h it is assured that when the cell support 1 is fixed in the holding device 2, the holding device 2 with the fixing ring 4 never stands on top of a base, etc. and thereby causing pressure to be exerted on the cell support 1.

Figure 2:
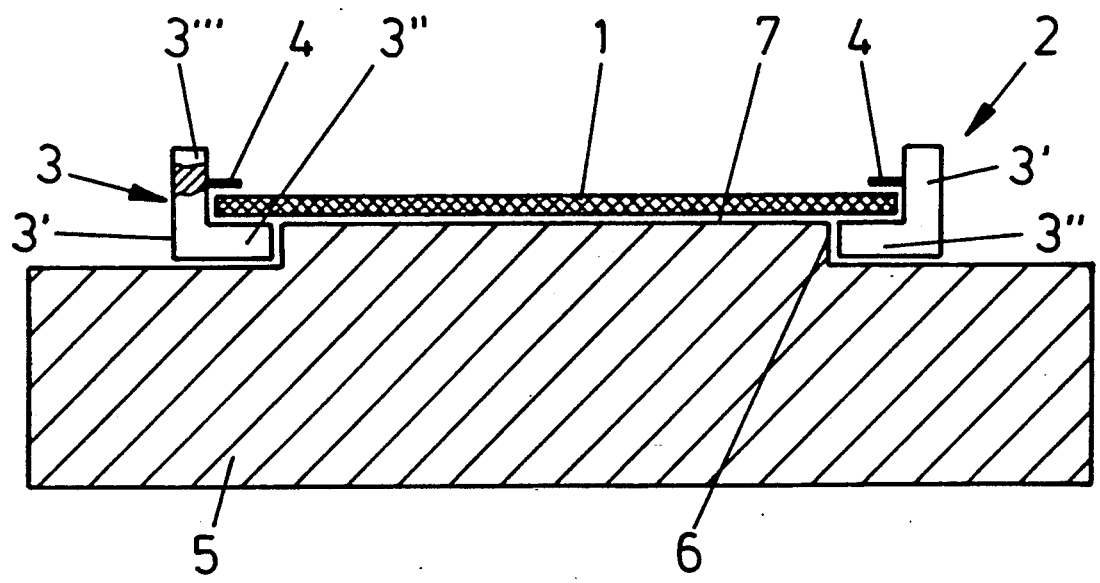
FIG. 2 is a cross-sectional view of the holding device and of a cell support for the cells during assembly with the use of a mounting aid or mounting block.

The above-described assembly is carried out in the manner shown in FIG. 2 with the use of a mounting block 5 which has on its upper side a circular-cylinder-shaped projection 6 with plane surface 7. The respective supporting ring 3 with its section 3" facing downward is placed on the mounting block 5 in such a way that the projection 6 is encircled by the section 3" and the surface 7 lies substantially in one plane with the then upper surface of the section 3". The cell support 1 is then inserted in the supporting ring 3 from above and fixed in the manner described above. Use of the mounting block 5 during the assembly ensures a plane bearing surface for the cell support 1, so that during the assembly the latter can be placed on flat and will not be damaged. In case of use (particularly FIGS. 3 and 4) the respective holding device 2 is turned by 180°, i.e. it is used with the section 3" lying above.

In the embodiment shown the inside diameter of the fixing ring 4 is smaller than the inside diameter of the section 3". This ensures that in every case the underside of the cell support 1 is accessible in that region where cultivation of the cells 8 takes place on the upper side of the cell support 1.

Figure 3:
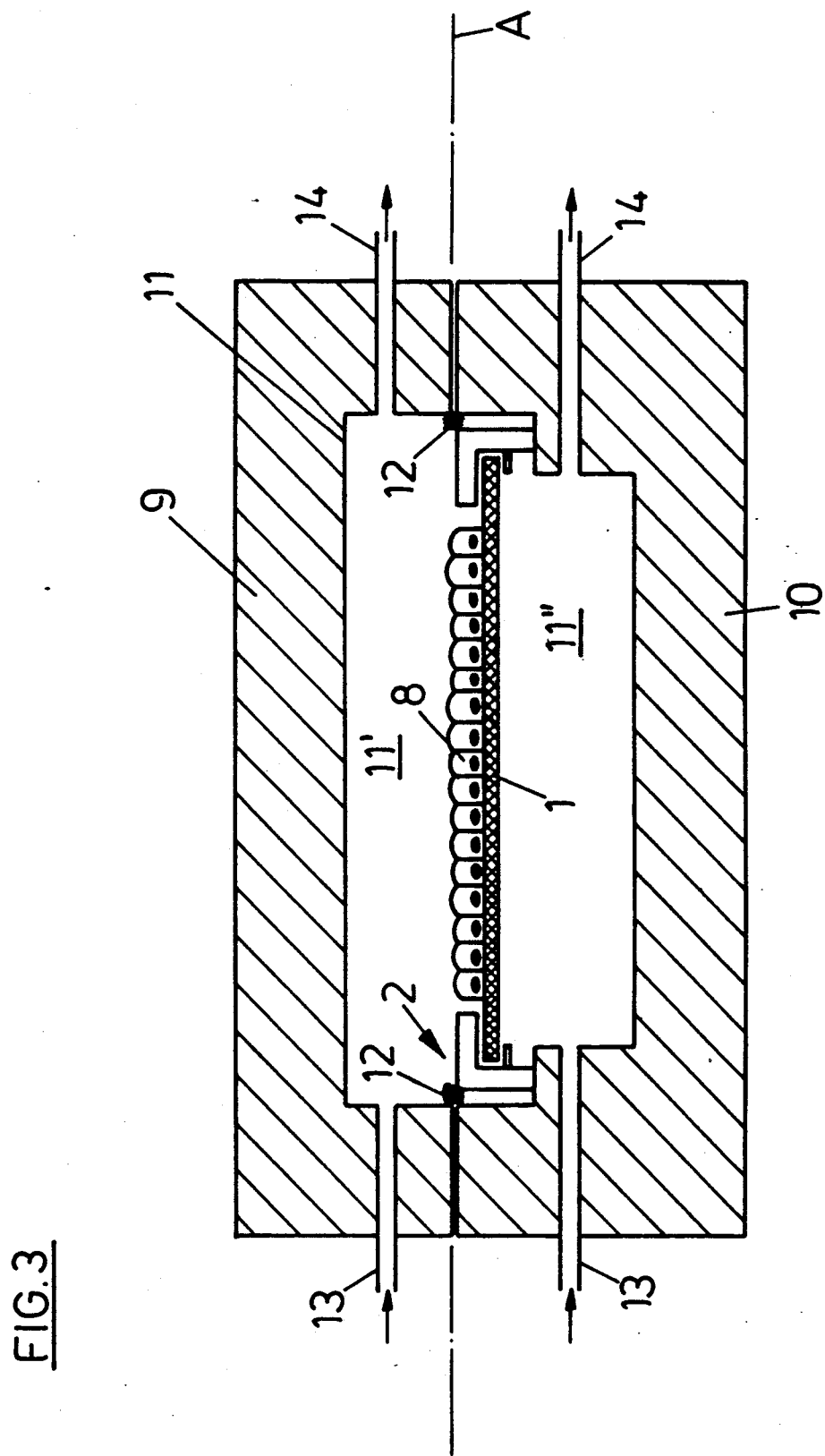
FIG. 3 is a simplified representation in cross-sectional view of a first possible embodiment of the apparatus of the invention as perfusion culture vessel.

The apparatus shown in FIG. 3 for a continuous perfusion consists of a culture vessel formed essentially of two basin-like receptacle halves 9 and 10 which, when the vessel is closed, form between them a chamber sealed off from the outside, or a corresponding inner space 11. Placed in this inner space 11 are the holding device 2 and the cell support 1 fixed in the latter, with the use of a gasket 12 between the holding device 2 and the inner surface of the receptacle halves 9 and 10. In this way the inner space 11 is subdivided into two partial spaces 11' and 11" which are separated from one another. Provided for the partial space 11' are the apical inflow opening 13 and apical outflow opening 14, and for the partial space 11" the basal inflow opening 13 and basal outflow opening 14. As a result of this construction a separate apical and basal perfusion of the cells 8 is made possible concurrently with an electrophysiologic recording of transport processes in presence of the smallest dead space. To this end the inflow openings 13 and outflow openings 14 are each constructed as electrodes in the form of tubules made of electrically conductive material. The lateral gasket 12 of the holding device 2 can very easily prevent any leaks in the special cell culture apparatus. This makes it possible to measure transport processes by electric or electronic derivation between the apical and basal side. In addition, by means of an individual apical and basal perfusion with hypotonic or hypertonic media it is possible during cultivation or during the experiment to bring about the formation of a gradient, such as occurs e.g. in the kidney. This type of utilization of cultivated cells is unique and opens up a new field in the science of cell biology, one that has not been possible so far in this art.

A further seal is provided between the receptacle halves 9 and 10 in the form of a packing ring 12', by means of which the inner space 11 is sealed off from the exterior. As FIG. 3 already shows, the recess forming the partial space 11' in the receptacle half 9 has a diameter that is smaller than the diameter of the supporting ring 3, so that upon closing the receptacle or culture vessel the holding device 2 placed in the recess of the receptacle half 10 is necessarily pressed onto the seal or the packing ring 12. The receptacle halves 9 and 10 are connected pivotably around axis A. A further particular advantage of the apparatus shown is that tubes (not shown in detail) connected to the inflow openings 13 or outflow openings 14 for the inlet and outlet of the treatment medium, respectively, need not be removed during the opening and closing of the culture vessel.

Figure 4:
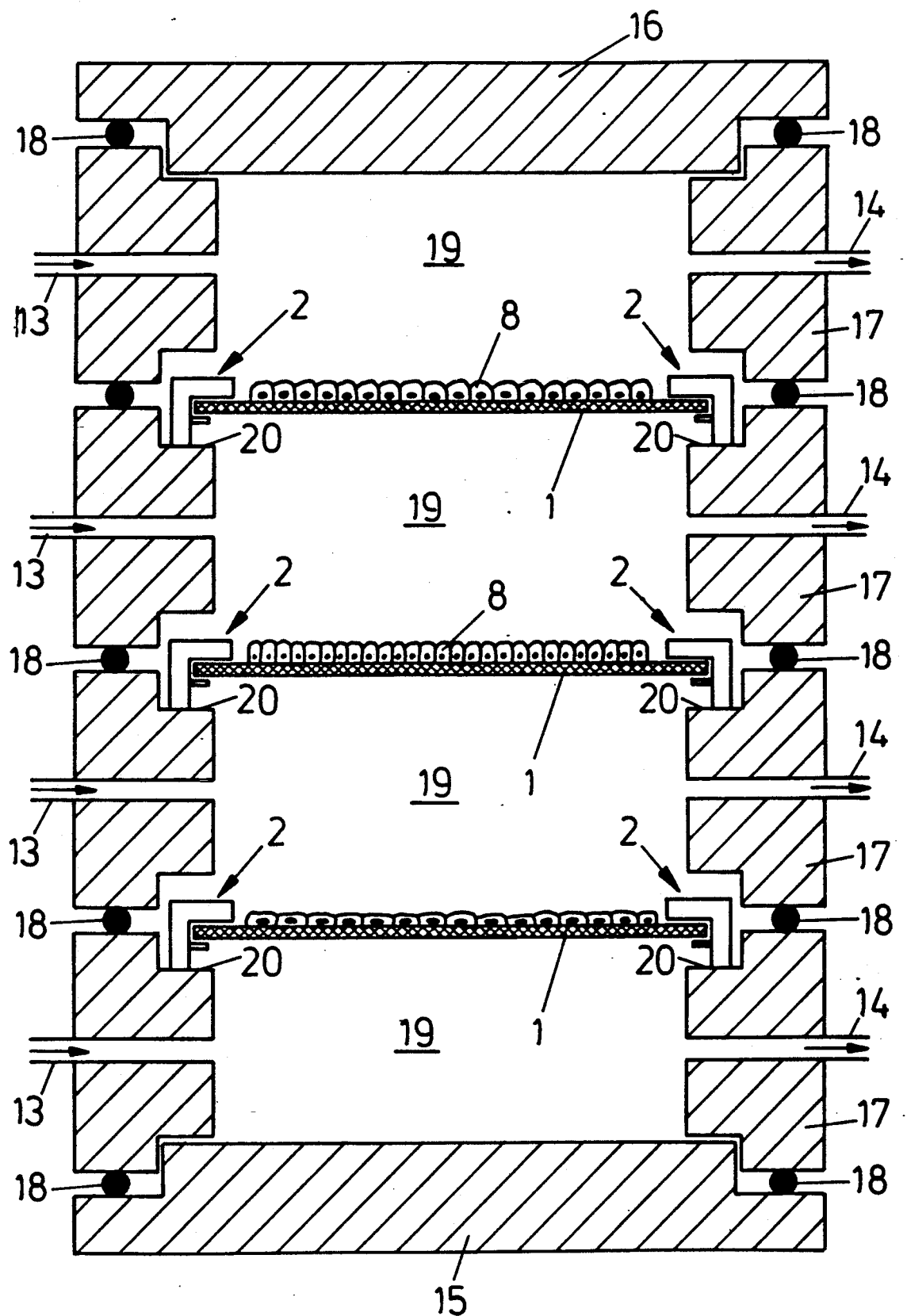
FIG. 4 is a simplified representation in cross-sectional view of another possible embodiment of the apparatus of the invention as bioreactor.

FIG. 4 shows another particular embodiment of the invention (bioreactor) for continuous perfusion. In this embodiment the culture vessel consists essentially of a base 15 and a cover 16, of a plurality of receptacle rings 17 and of packing rings 18 arranged between the latter. Each receptacle ring 17 has an inflow opening 13 and an outflow opening 14 for a treatment medium. In the embodiment shown in FIG. 4 a total of four receptacle rings 17 coaxially arranged above one another form the culture vessel, whose inner space 19 is closed on top by the cover 16 and at the bottom by the base 15. In the inner space 19 three holding devices 2, each with a cell support 1, are arranged one on top of the other in a stacked manner. To this end the receptacle rings 17 form supports 20 for the holding devices 2, so that each holding device 2 is kept at a distance from the adjacent holding device by means of a receptacle ring 17, and the uppermost and lowest holding devices 2 are kept at a distance from the cover 16 and base 15, respectively, by means of a receptacle ring 17.

By using an appropriate number of receptacle rings 17 the stack height or number of the holding devices 2 may be chosen arbitrarily. In principle it is also possible to use holding devices 2 having different diameters, in which case the receptacle rings 17, too, will have an inside diameter adapted to the respective diameter of the holding devices 2.

In the apparatus shown in FIG. 4, too, the cell supports can be perfused from the apical and from the basal side. The apparatus according to FIG. 4 has the particular advantage of having an extremely small dead space. It is possible either to introduce cell supports 1 with similar types of cells 8 into the apparatus or use cell supports 1 with different cell types grown thereon, whereby, under certain conditions, a positive mutual influencing of the cell types can be effected.

The apparatus according to FIG. 4 has also the advantage that each individual cell support 1 can be individually checked in the apparatus. This can be done because each cell support 1 has, from the apical and basal sides, an inlet of treatment medium through the inflow opening 13 and an outlet of treatment medium through the outflow opening 14. As a result e.g. Each cell support 1 can be separately checked for an infection or secretion. The tubular culture vessel (reactor tube) of the apparatus can be readily opened by removing the cover 16 or one or more receptacle rings 17. so that each desired cell support 1 with the respective holding device 2 can be taken out or replaced individually.

Figure 5:
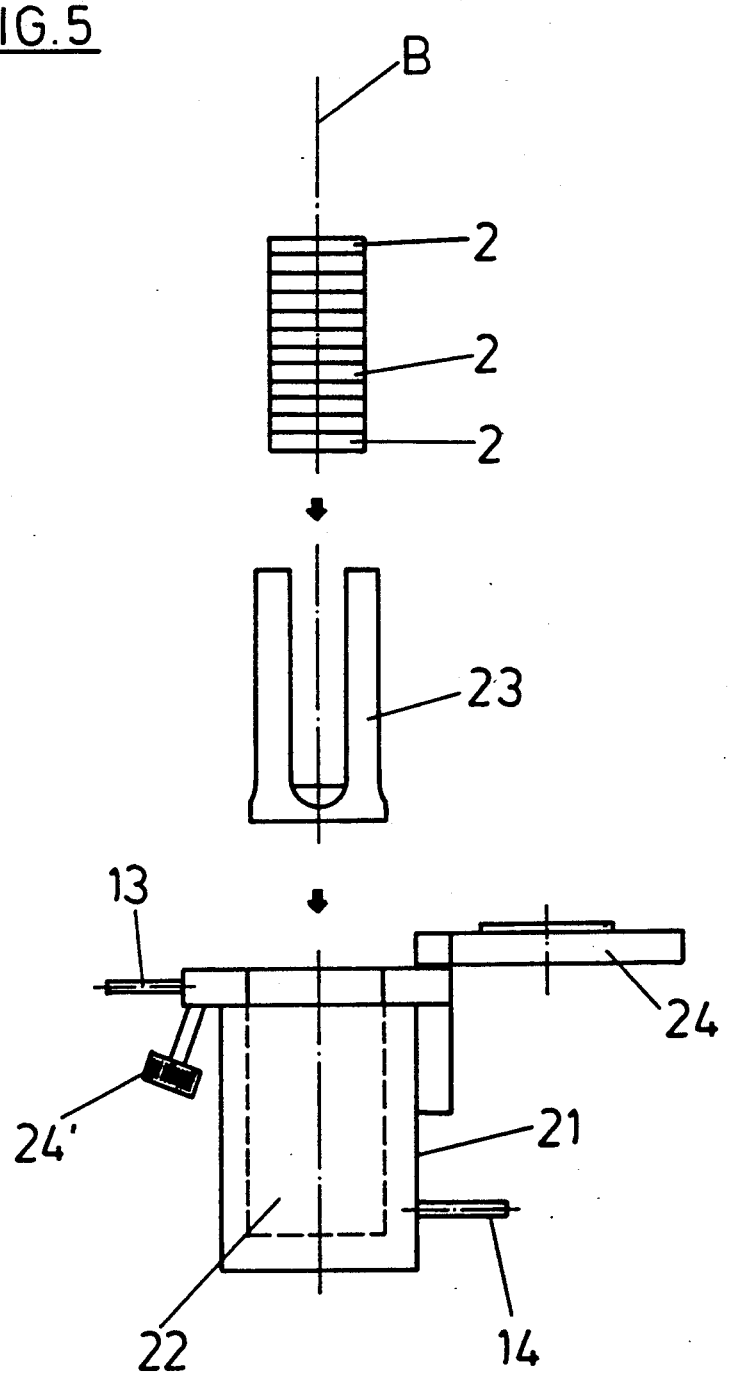
FIGS. 5 and 6 show, in simplified representation and partly in cross-sectional view, further possible embodiments of the apparatus of the invention.

FIG. 5 shows an apparatus consisting essentially of a cup-like culture vessel or receptacle 21. The receptacle 21 has an inner space 22 which is of circular cylindrical shape with respect to an axis B which perpendicularly intersects the plane of the open side of the inner space 22. Into the inner space 22 a basket 23 can be placed in which several holding devices 2 with one cell support 1 each can be arranged in a stacked manner in the direction of the axis B. After introduction of the basket 23 with the cell supports 1 or holding devices 2, the inner space 22 is tightly closed by the cover 24 hinged at the receptacle 21, using a closing mechanism consisting of a closing screw 24'. The inflow opening 13 is situated in the region of the inner space opening 22 closable by the cover 24. The outflow opening 14 is provided in the region of the bottom of the inner space 22. Also, the arrangement of inflow opening and outflow opening can be interchanged.

After the above-described introduction of the cell support 1 and closure of the receptacle 21 the latter is tilted by 90° from the position shown in FIG. 5, so that the axis B will extend in the horizontal direction. Since the axial dimension of the basket 23 is somewhat greater than the height of the largest stack of holding devices 2 that can be placed in said basket, distances will arise between the individual holding devices when the closed receptacle 21 is tilted, so that the respective treatment medium can act from both sides on each cell support 1.

Figure 6:
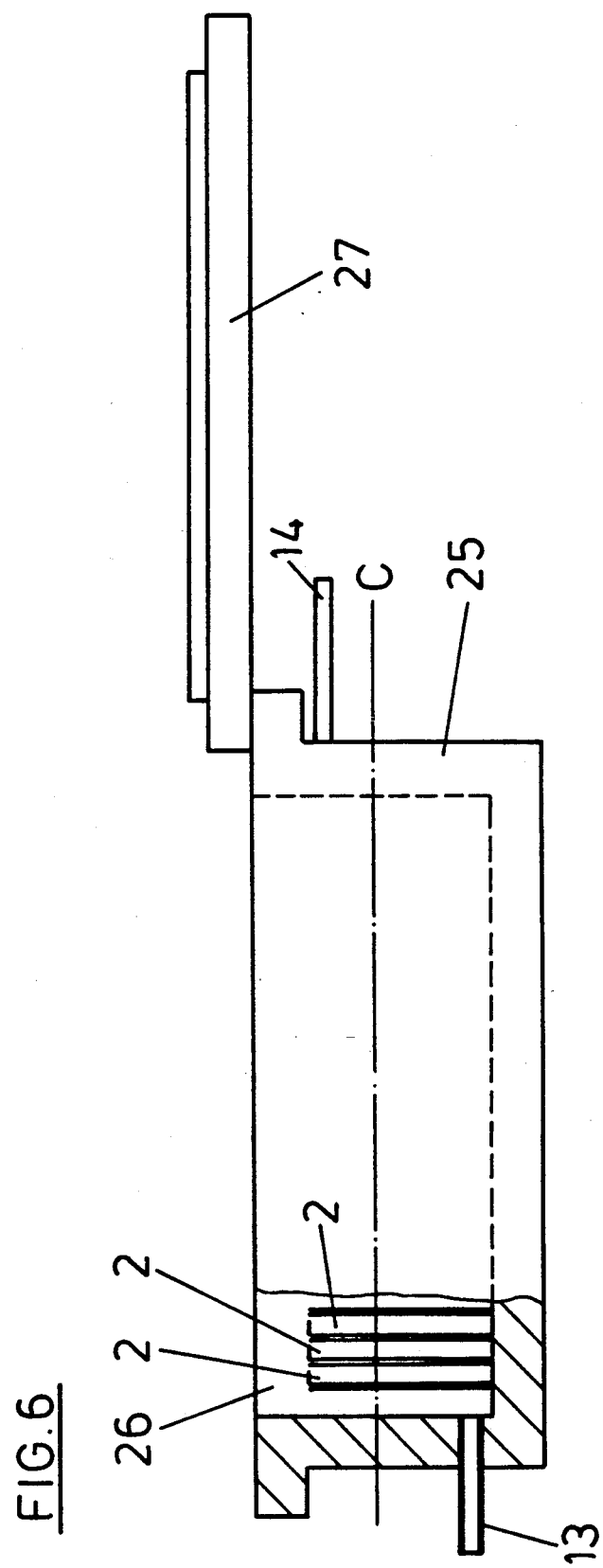

FIG. 6 shows an embodiment with a culture vessel or receptacle 25 having an inner space 26 such that a plurality of holders 2 with cell supports 1 can be placed therein in succession in a substantially horizontal direction C, in such a way that the planes of the frames of the frame-like holders 2 and of the cell supports 1, respectively, are situated essentially in vertical planes perpendicular to the axis direction C. The holding devices 2 are placed either directly in the receptacle 25 or in a basket which is then introduced into the receptacle 25 together with the holding devices 2 and the cell supports 1. It is preferably ensured by means of spacers provided on the inner surfaces of the receptacle 25 or on the basket that adjacent holders 2 are always at a distance from one another, and that the holders are also at a distance from the inner surfaces of the receptacle 25.

The receptacle 25 is open at its upper side, i.e. a side that is parallel to the axial direction C, and can there be closed by means of a hinged cover 27. The inflow opening 13 is provided on a front side of the receptacle 25 extending essentially perpendicularly to the axial direction C, and the outflow opening 14 on the other front side extending essentially perpendicularly to the axial direction C, the outflow opening 14 being preferably arranged in the region of the upper, open side of the inner space 26, and the inflow opening 13 preferably in the region of the bottom of the inner space 26.

Even in the embodiments according to FIGS. 5-6 the inflow openings 13 and outflow openings 14 again preferably consist of pipe pieces or tubules made of electrically conductive material, which can then be used as electric probes. Moreover, the devices according to FIGS. 4-6 have the advantage that so-called "nursing" cells can be cultivated on a few cell supports 1, in order to favorably influence the growth of the cells 8 on the rest of cell supports 1.

As indicated by 3''' in FIG. 2 the supporting ring 3 is provided on its front side facing away from the section 3'' with a plurality of recesses or indentations 3''' which are open both toward said front side and toward the inner and outer side of the section 3'. In the case of holding devices 2 stacked one on top of the other these recesses or indentations 3''' create openings for the passage of the treatment medium.

I claim:

1. An apparatus for cultivation of biological cells, comprising:
   a culture vessel defining an internal space (11, 19, 22, 26);
   at least one inflow opening (13) communicating with said internal space for introducing a cell treatment medium;
   at least one outflow opening (14) communicating with said internal space (11, 19, 22, 26) for removing said cell treatment medium;
   at least one holding device (2) arranged to support a penetrable flat cell substrate (1) with a cell culture thereon and being removably installed in said internal space such that the holding device rests on a surface inside the internal space and the cell treatment medium can come into contact with said cell substrate (1) from both the apical and basal sides;
   said holding device (2) comprising a supporting ring (3) and a fixing ring (4), said supporting and fixing rings being concentric, and with the cell substrate being fixed between these rings (3, 4);
   the supporting ring (3) having a supporting ring section (3') encircling said fixing ring (4) and said supporting ring section having an axial height (h);
   the fixing ring (4) having an axial thickness, the axial thickness of the fixing ring being sufficiently smaller than the axial height (h) of said supporting ring section (3') such that the fixing ring (4), when positioned in said supporting ring, is incapable of abutting the said surface of the internal space of the holding device (2).

2. The apparatus of claim 1 wherein the axial thickness of the fixing ring (4) is less than half of the axial height of the supporting ring section.

3. The apparatus of claim 1 wherein said supporting ring (3) has an inwardly directed annular flange section (3'') on one side of said supporting ring section (3'), with the cell support (1) being clamped between said axially directed annular flange section (3'') and the fixing ring (4), said supporting ring (3) being further provided with a plurality of recesses (3''') on the face opposed to said inwardly directed annular flange section (3'').

4. The apparatus of claim 1 wherein the cell substrate (1) is coated with a matrix material selected from the group consisting of cellular and extracellular.

5. The apparatus of claim 4 wherein there is a plurality of holding device (2), each supporting a cell substrate (1), at least one of the holding devices (2) having a cell substrate with a different coating from the coating on a cell substrate in at least one other holding device.

6. The apparatus of claim 1 wherein a plurality of holding devices (2), each supporting a cell substrate (1), is successively arranged in said internal space (19).

7. The apparatus of claim 6 wherein the culture vessel comprises at least two receptacle rings (17) coaxially arranged one above the other, a base (15) and a cover (16), said receptacle rings, said base and said cover defining said internal space.

8. The apparatus of claim 6 wherein the culture vessel comprises at least two receptacle rings (17) coaxially arranged one above the other, a base (15) and a cover (16), said receptacle rings, said base and said cover defining said internal space, and wherein each receptacle ring (17) has an inflow opening and an outflow opening.

9. The apparatus of claim 6 further comprising a basket (23) for receiving said plurality of holding devices (2), said basket being removably installed in said internal space.

10. The apparatus of claim 1 wherein a plurality of holding devices (2), each supporting a cell substrate (1), a successively arranged in said internal space (19) and wherein an inflow opening (13) and an outflow opening (14) are provided for each said cell substrate.

11. The apparatus of claim 1 wherein a plurality of frame-like holding devices (2), each supporting a cell substrate (1), is successively arranged in said internal space (22, 26), said internal opening having at least one inflow opening (13) and at least one outflow opening (14).

12. The apparatus of claim 1 wherein said culture vessel comprises a receptacle (21) with an openable cover (24), said cover openable closing said internal space (22) of the receptacle (21) on a side extending parallel to the axial direction (C) of the at least one holding device (2).

13. The apparatus of claim 1 wherein there is a plurality of holding devices (2) at least one of which has a different diameter from at least one other.

14. The apparatus of claim 1 wherein said at least one of said inflow and outflow openings functions as an electrode.

15. The apparatus of claim 14 wherein said at least one of said inflow openings and outflow openings is composed of electrically conductive material.

* * * * *

UNITED STATES PATENT AND TRADEMARK OFFICE
CERTIFICATE OF CORRECTION

PATENT NO. : 5,190,878
DATED : March 2, 1993
INVENTOR(S) : Wilhelm Minuth

It is certified that error appears in the above-identified patent and that said Letters Patent is hereby corrected as shown below:

On title page, item [19] "Wilhelm" should read --Minuth--
Title page, item [76]
    Change the inventor's name to --Wilhelm Minuth--.

Column 2, line 34, change "ting" to --ring--.

Column 4, line 27, change "Each" to --each--.

Column 6, line 9 (claim 3), change "axially" to --inwardly--.

Column 6, line 18 (claim 5), change "device" to --devices--.

Column 6, line 54 (claim 12), change "cover openable" to --openable cover--.

Signed and Sealed this

Sixteenth Day of November, 1993

*Attest:*

BRUCE LEHMAN

*Attesting Officer*    *Commissioner of Patents and Trademarks*